(12) United States Patent
Ruffenach

(10) Patent No.: US 6,173,237 B1
(45) Date of Patent: *Jan. 9, 2001

(54) OPTIMIZATION PROCESS OF A BITUMEN/POLYMERS MIXTURE

(75) Inventor: Francois Ruffenach, Rouen (FR)

(73) Assignee: Onduline, Paris (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/150,191

(22) Filed: Sep. 10, 1998

(30) Foreign Application Priority Data

Sep. 12, 1997 (FR) .................................................. 97 11406

(51) Int. Cl.⁷ ...................................................... G01F 1/12
(52) U.S. Cl. ............................................................ 702/100
(58) Field of Search ........................... 524/59, 70; 73/73; 702/100, 32, 117

(56) References Cited

U.S. PATENT DOCUMENTS

| | | | |
|---|---|---|---|
| 3,853,800 | * 12/1974 | Haberl | 524/70 |
| 3,887,422 | * 6/1975 | Bosniack | 524/70 |
| 3,917,895 | * 11/1975 | Bosniack | 524/70 |
| 3,960,793 | * 6/1976 | Bosniack | 524/70 |
| 4,357,169 | 11/1982 | Trujillo | 106/284 |
| 5,326,798 | * 7/1994 | Danese | 524/70 |
| 5,365,793 | 11/1994 | Terrel et al. | 73/813 |
| 5,659,140 | 8/1997 | Jakob et al. | 73/790 |

FOREIGN PATENT DOCUMENTS

| | | |
|---|---|---|
| 39 08 831 | 9/1989 | (DE) . |
| 2 244 131 | 11/1991 | (GB) . |

* cited by examiner

Primary Examiner—Hezron Williams
Assistant Examiner—Jay L. Politzer
(74) Attorney, Agent, or Firm—Young & Thompson

(57) ABSTRACT

A method of producing roofing sealing material and roofing sealing material models includes producing a number of bitumen/polymers mixtures holding the polymers and bitumen identical in all of the mixtures and varying the respective percentages of the polymers from mixture to mixture.

10 Claims, No Drawings

OPTIMIZATION PROCESS OF A BITUMEN/POLYMERS MIXTURE

BACKGROUND OF THE INVENTION

The invention relates to the manufacture of bitumen/polymers mixtures, notably designed for the production of roofing sealing membranes.

DESCRIPTION OF THE RELATED ART

The polymers used in these mixtures can be of various natures. Recycled polymers or polymers in the form of waste are classically used in order to reduce the cost of raw materials.

We can also mention the APP (atactic polypropylene) which constitutes a manufacture waste of the IPP (isotactic polypropylene).

The physical characteristics of these recycled polymers are not constant. Still, the manufacturers of sealing membranes must respect the technical specifications and guarantee the quality of their products.

The manufacturers have only empirical means in order to forecast the physical characteristics of a bitumen/polymers mixture, when the quantity of the polymers is caused to vary or when the nature of the polymers is modified.

For each new polymer or for each new delivery of a recycled polymer or of a polymer in the form of waste, the manufacturers must perform tests in order to adjust the quantity of polymers in the mixture. Moreover, in practice, the polymers are used in excess in order to guarantee the quality of the finished product, which increases the costs. Finally, frequent and expensive quality checks are necessary.

When a quality check shows that the characteristics of the bitumen/polymers mixture do not comply with the technical specifications, once again empirical means are implemented to correct the mixture, among other things by incorporating additional quantities of polymers.

In the relatively old technical field of sealing membranes, these empirical means for determining bitumen/polymers mixtures are the only ones to be used. The number of tests is also limited not to block the production.

The implementation of more rational methods is, generally, rejected, taking into account the risks of slowing down the manufacture.

SUMMARY OF THE INVENTION

The purpose of the invention is to remedy these shortcomings while offering a process to determine the influence of the percentage of the different polymers of a bitumen/polymers mixture on at least one physical characteristic of the mixture, on the basis of a limited number of tests which are carried out to establish a reference model, for the polymers and the bitumen under consideration.

Thus, the process according to the invention consists in:
performing a limited number of bitumen/polymers mixtures, according to the test schemes method, whereby the polymers and the bitumen are identical in all the mixtures and whereas the respective percentages of the polymers can be set to a maximum level or to a minimum level, of a range of values to be determined in advance for each of them, measuring the said physical characteristic(s) for each of the said mixtures, and deducing, by statistical calculations, a modelling of the said physical characteristic(s).

The process according to the invention exhibits the advantage of being able to take into account the influence of another polymer, which would be introduced into the mixture.

The process then consists moreover in:
performing at least four additional mixtures incorporating another polymer, measuring the said physical characteristic(s) for each of these additional mixtures, and deducing the changes to make to the modelling of the said physical characteristic(s), to take into account the introduction of this other polymer.

The process according to the invention is not limited to the introduction of a single other polymer, whereas the previous phases of the process can be repeated for any other polymer which should be introduced into the mixture.

The bitumen/polymers mixture can contain fillers. The percentage of fillers in the mixture may be constant.

The physical characteristic(s) of the mixture is (are) notably flexibility at low temperature in mint condition and in aged condition, Brookfield viscosity at 180° C., penetration at 25° C. and 60° C. and/or softening temperature.

As regards the manufacture of sealing membranes, the polymers of the said bitumen/polymers mixture are selected, for exemplification purposes, among the APP, IPP and the copolymers of ethylene/propylene type.

The invention also relates to a process for the determination of at least one physical characteristic of a bitumen/polymers mixture according is to the polymers used.

This process consists in:
implementing the process according to the invention for determining the influence of the percentage of the different polymers of the mixture on the said physical characteristic(s), and fixing the percentages of each polymer in order to derive the value of the said physical characteristic(s).

The invention also relates to a process for obtaining a bitumen/polymers mixture exhibiting one(several) desirable physical characteristic(s) of the mixture The process consists in:
implementing the process according to the invention for determining the influence of the percentage of the different polymers of the mixture in the said physical characteristic(s), fixing a range of values for the said characteristic(s) and deriving the percentage of each polymer in the mixture.

This process consists in determining the percentages of the polymers while taking their cost into account.

These processes enable to maximize the bitumen/polymers mixtures in terms of quality and of cost of raw materials, while remaining fast and cheap to be implemented.

The invention also relates to a process for modifying a bitumen/polymers mixture exhibiting one (several) determined physical characteristic(s) to be modified.

This process consists in:
implementing the process according to the invention to determine the influence of the percentage of the different polymers of the mixture on the said physical characteristic(s), fixing other values of the said physical characteristic(s) of the said mixture and calculating the additional quantity of at least one polymer to be added to the said mixture so that it exhibits physical characteristics of values more or less equal to these other values.

All these processes call for prior determination of the influence of the different polymers on the mixture, but their implementation does not require any complementary test during manufacture.

The invention will be understood better and other aims, advantages and characteristics of the former will appear more clearly when reading the detailed description, which follows.

Maximization of the bitumen/polymers mixtures requires knowing the influence of each of the constitutive parts of the mixture on the physical characteristics of the former.

The physical characteristics adopted are for instance imposed by standards or classically selected by the manufacturers.

The following can be mentioned, among others:

flexibility at low temperature (expressed in degrees Celsius) in mint condition and in aged condition (after 4 weeks at 80° C.), measured according to a so-called UEATC (Union Européenne des Agréments Techniques de la Construction—European Union of the Technical Building Permits), Brookfield viscosity at 180° C. (expressed in centipoises), measured with a rotary viscometer (pointer 28, speed 50 rpm), penetration at 25° C. and at 60° C. (expressed in deci mm), measured according to the standard NFT 66-004, softening temperature (expressed in degrees Celsius), measured according to the standard NFT 66-008.

Inasmuch as the physical characteristics of the polymers-modified bitumen depend on the nature of each polymer and on its percentage in the mixture, as well as on the bitumen selected, the theoretical number of tests is enormous in order to establish sound modelled physical characteristics. This acts as a deterrent for the man of the art and this is the reason why no model has been developed in this technical field.

DESCRIPTION OF THE PREFERRED EMBODIMENT

The invention uses a so-called test-scheme method, which enables to reduce the number of tests to be performed in order to model the physical characteristics of the mixture, while enabling one to obtain reliable models. Moreover, this method makes obvious the interactions between the different polymers.

In this context, we can refer to the book by J. GOUPY. "la mémethod des plans d'expériences" (the test-scheme method), published by the Editions Dunod in October 1988.

The application of this method in the field of the bitumen/polymers mixtures is now going to be described.

The physical characteristics modelling of the mixture is established for a given bitumen.

The bitumen considered here exhibits the following characteristics:

|  | BITUMEN |
| --- | --- |
| Softening temperature (° C.) | 44.0 |
| Penetration at 25° C. (mm/10) | 112 |
| Viscosity at 135° C. (mm²/s) | 290 |

Its composition is as follows:

|  | Bitumen |
| --- | --- |
| Asphaltenes | 16.3 |
| Resins | 19.9 |
| Aromatics | 55.7 |
| Saturated | 8.1 |

In this example, the bitumen/polymers mixture is filled with mineral fillers, whose percentage in the mixture is by approximation 18%.

The polymers composing a modified bitumen are generally not constituted of a single product.

They often comprise different IPP and APP as well as copolymers.

In the example described here, 6 polymers have been adopted;

whose characteristics are as follows:

| IPP | Very hard and resistant polymer whose melt flow index is in the order of 8 |
| --- | --- |
| APP1 | Brookfield viscosity at 180° C. ~ 500 CP<br>And penetration at 25° C. ~ 10–20 mm/10 |
| APP2 | Brookfield viscosity at 180° C. ~ 3000 CP<br>And penetration at 25° C. < 10 mm/10 |
| COPO1 | Brookfield viscosity at 180° C. ~ 1,000,000 CP<br>Good flexibitity at low temperatures |
| COPO2 | Brookfield viscosity at 180° C. ~ 700,000 CP<br>Harder and tess flexible than COPO1 |
| COPO3 | Brookfield viscosity at 180° C. ~ 800,000 CP<br>Harder and less flexible than COPO2 |

The test scheme is based upon six independent variables: IPP (in %), APP1 (in %), APP2 (in %), COPO1 (in %), COPO2 (in %) and COPO3 (in %). Thus, 64 mixtures must be performed (whereas the bitumen and the charges are kept identical in their nature, the percentage of charges in this example is kept constant and the percentage of bitumen is the complement to 100% of the total percentage of polymers and of charges) and for each of them, the following are measured: softening temperature (TR), penetration at 25° C. (Pen 25° C.) and 60° C. (Pen 60° C.), Brookfield viscosity at 180° C. (Visc 180° C.) and flexibility at low temperature, in mint condition (FBT) and in aged condition ($FBT_4$).

The percentage of polymers in the modified bitumen is generally comprised between approx. 19 and 26% in weight, whereas the remaining is composed of bitumen and of fillers. In this range, the mixture has the form of a continuous polymer phase in which the bitumen is dispersed.

Prior studies having shown that many interactions could be neglected, the number of mixtures is reduced to 16.

16 mixtures are performed, whereby each mixture comprises a minimum or maximum percentage of each of the 6 polymers, corresponding to a maximum level and to a minimum level of a range of values determined in advance for each polymer.

For instance, one of these mixtures will comprise a maximum level of IPP, APP2 and COPO1 and a minimum level of APP1, COPO2 and COPO3.

Also, for exemplification purposes, the value ranges of each polymer are as follows (% in weight):

| IPP: | 2.5–3.5% | COPO1 | 2.8% |
| APP1: | 6.3% | COPO2 | 1.3% |
| APP2: | 6.2% | COPO3 | 1.7% |

Complementary mixtures have also been performed, while using the mean percentage of each polymer in order to check the models for linearity and to control the reproducibility of the measuring methods. In total, 20 have been performed this way.

Statistical evaluations can be performed using a Stat Graphics Plus 1.1 type software.

Using this computer tool, the results of the measurements obtained for each of the physical characteristics and for each of the 20 bitumen/polymers mixtures, enable one to easily model the different physical characteristics.

In the example described here, the models obtained are as follows while using standardised notation in −1 and +1 of the variables:

(1) TR: $153.1 + 0.92 \cdot IPP + 0.33 \cdot APP1 + 0.24 \cdot COPO3 + 0.22 \cdot IPP \cdot COPO2$ (2) $Pen_{25° C.}$: $35 - 2.13 \cdot IPP - 0.56 \cdot APP1$ (3) $Pen_{60° C.}$: $147 - 19.5 \cdot IPP - 5.9 \cdot APP1 - 0.14 \cdot IPP \cdot APP1$ (4) $Ln(Visc_{180° C.})$: $7.89 + 0.087 \cdot IPP + 0.028 \cdot APP1 + 0.13 \cdot COPO1 + 0.096 \cdot COPO2 + 0.083 \cdot COPO3 + 0.011 \cdot IPP \cdot APP1 + 0.011 \cdot IPP \cdot COPO2$ (5) FBT: $-15 + 0.69 \cdot IPP - 0.69 \cdot APP2 - 0.81 \cdot COPO1$ (6) $FBT_4$: $-10.2 + 1.44 \cdot IPP - 0.94 \cdot APP2 - 0.94 \cdot COPO1 - 1.19 \cdot COPO2$ The constant which appears in each model provides with an estimate of the corresponding physical characteristic of the mixture, for a formulation of polymers comprising mean values.

When the effect of a polymer on the leading constant of the models (1) to (6) is negligible, the polymer does not appear in the model. Besides, the method used enables to put in evidence possible interactions amongst the polymers.

These models show that the softening temperature and the penetration at 25 and 60° C. depend essentially on the quantity of IPP, whereas the viscosity and the flexibility are influenced by practically all the polymers, whereas the percentage of each polymer varies over the ranges indicated previously.

For an example of mixture, the values of the physical characteristics forecast by the models will be specified, as well as the measured values of the same physical characteristics.

The percentages in weight of the polymers in the example at hand (already indicated previously) are as follows:

| IPP: | 3.5% | COPO1 | 1.7–2.8% |
| APP1: | 6.3–8.7% | COPO2 | 1.3–2.4% |
| APP2: | 4.8–6.2% | COPO3 | 1.7–2.8% |

For this example, the values of the physical characteristics, given by the models (1) to (6) are as follows:

TR: 153.2° C. $Visc_{180° C.}$: 2,640 CP $Pen_{25° C.}$: 33.4 deci mm FBT: −15.8° C.

$Pen_{60° C.}$: 133 deci mm $FBT_4$: −9.5° C.

The measured values of the same physical characteristics are:

TR: 153.5° C. $Visc_{180° C.}$: 2,684 CP $Pen_{25° C.}$: 33 deci mm FBT: −15° C.

$Pen_{60° C.}$: 131 deci mm $FBT_4$: −9° C.

This example shows that the models (1) to (6) are reliable. This has also been confirmed by the numerous tests carried out.

The models, such as previous (1) to (6), exhibit moreover another considerable advantage.

They can be modified easily in order to take into account another polymer. For example, if one of the copolymers which have been used to define the model has been deleted from stock and is replaced with a new copolymer or if the manufacturer receives a new batch of one of the APP, the models developed previously are not useable directly. However, it is not necessary to reschedule a test scheme and to perform the whole set of measurements again, for all the physical characteristics, in order to establish new models.

To determine the influence of the new constitutive part, it has been established that a limited number of mixtures, minimum 4, and of the measurements of the physical characteristics to be modelled, were sufficient.

The composition of the mixtures with the new constitutive part has been selected as during the preparation of the initial model, while adopting a maximum percentage, a minimum percentage and an intermediate percentage.

The results obtained enable to modify simply, quickly and cheaply to the model established initially in order to integrate the new polymer.

The modifications that can be made are not limited to the introduction of a single polymer into the models.

Therefore, the manufacturer can be very easily provided with models suited to the products which he keeps effectively For example, if one of the polymers has been deleted from stock, the model remains valid, it suffices to adjust the quantities of the other polymers.

The models thus enable to determine the physical characteristics of a given mixture, in relation to the percentages of polymers used. The manufacturer can then decide to accept the mixture, according to whether its characteristics comply with the technical specifications which he is bound to respect without resorting to a specific mixture.

He can also determine rapidly how the quantities of each polymer must be modified in order to comply with the technical specifications.

This constitutes a considerable advantage with respect to the classical methods used today and which are mainly empirical; each time we want to modify the quantity of a polymer (for example: addition of a new polymer, adjustment of a physical characteristic of the mixture, polymer out of stock), the manufacturer proceeds by trial and error while performing at least one or two mixtures in his laboratory to make sure that the physical characteristics of the mixture do comply with the technical specifications. The frequency of these modifications can be greater than once a day.

Finally, these empirical methods are relatively unreliable. The manufacturers, therefore, have a tendency to overdose the polymers in the mixture. However, this overdosing is detrimental to the cost of the mixtures and hence to that of the sealing membranes.

The manufacturer can also use the models for optimization of the mixture, while determining the percentages of each polymer in relation to physical characteristics of a given value and while possibly integrating cost elements or manufacturability parameters (for instance the nature of the reinforcement armatures used).

Thus, the manufacturer only needs to perform a limited number of tests once for all. On the basis of established models, he can prepare new formulations of the mixture, for a given bitumen, complying with particular specifications. No other test is necessary.

This constitutes an advantage in relation to the classical empirical methods which call for new tests systematically when the specifications regarding the physical characteristics of the mixture are modified.

The invention also comprises advantages for controls during manufacture.

The manufacturers perform these controls classically, notably while performing samples which are then analysed. If the tests show that the bitumen/polymers mixture does not comply with the technical specifications, the formulation of the mixture must be modified upstream, on the one hand, and the mixture already obtained must be corrected, on the other hand, so that it meets the specifications. This method is time-consuming and expensive to be implemented, while remaining subject to many uncertainties.

The invention enables first of all to remedy the possible manufacture deviations with respect to the technical specifications in quite a simple way.

Samples are made on the mixture manufactured.

The physical characteristics of the mixture are measured and compared to the theoretical values expected by using models or the technical specifications.

If a significant deviation is detected, the manufacturer conducts investigations. They put in evidence, for instance, an error in the charge of the bitumen or of one of the polymers. This error is therefore corrected immediately.

They also enable to correct easily the mixture already obtained, whereas constitutive elements are added. There again, the models previously established allow determining easily the correction to be made since they enable to anticipate the consequence of any added constitutive element.

For exemplification purposes, if the mixture obtained is not viscous enough, the model (4) enables to forecast easily the effect of a quantity change of a polymer, for instance IPP or COPO2.

The manufacturer can thus be provided, without resorting to any additional tests, with several solutions to correct the mixture. He will then perform a selection, notably on the basis of cost criteria.

It should be noted that the physical characteristics of a mixture are modelled for a defined bitumen. Comparison of the models established for several bitumens also provides the manufacturer with indications regarding the selection of the bitumen, in relation to the polymers used and to the physical characteristics requested.

Thus, the invention enables the manufacturer of bitumen/polymers mixtures to foresee the effects of a change in the composition of the polymers on the physical characteristics of the mixture. By knowing in advance the influence of each polymer, for a given bitumen, he can adapt the composition of the polymers, without resorting to any additional tests, and he can comply with the technical specifications to which he is subject.

What is claimed is:

1. A process for obtaining a bitumen/polymers mixture for the production of roofing sealing membranes, wherein the mixture exhibits a selected physical characteristic, and wherein the process comprises the steps of;

producing a number of bitumen/polymers mixtures wherein the polymers and the bitumen are identical in all the mixtures and wherein the respective percentages of the polymers and bitumen vary from mixture to mixture, measuring said physical characteristics for each of said mixtures, producing a model of the said physical characteristics in the form of:

TR=A+B*IPP+C*APP1+D*COPO3+E*IPP*COPO2,

Pen25° C.=F−G*IPP−H*APP1,

Pen60° C.=I−J*TPP−K*APP1−L*IPP*APP1,

Ln(Visc180° C.)=M+N*IPP+P*APP1+O*COPO1+R*COPO2+S*COPO3+T*IPP*APP1+U*IPP*COPO2,

FBT=V+W*IPP−X*APP2−Z*COPO1, and

FBT4=X+A1*IPP−A2*APP2−A3*COPO1−A4*COPO2, each of A, B, C, D, E, F, G, H, I, J, K, I, L, M, N, P, O, R, S, T, U, V, W, X, Y, Z, A1, A2, A3, and A4 being determinable constants, TR represents a softening temperature having units of degrees Celsius, IPP represents an isotactic Polypropylene expressed as a % weight of the total mixture, APP1 represents a first atactic polypropylene expressed as a percent weight of the total mixture, APP2 represents a second atactic polypropylene expressed as a percent weight of the total mixture, COPO1 represents a first copolymer expressed as a percent weight of the total mixture, COPO2 represents a second copolymer expressed as a percent weight of the total mixture, COPO3 represents a third copolymer expressed as a percent weight of the total mixture, Pen25° C. represents penetration at 25° C. expressed with units of deci mm, Pen60° C. represents penetration at 60° C. expressed with units of deci mm, Visc180° C. represents a Brookfield viscosity at 180° C. expressed with units of CP, FBT represents flexibility at a low temperature in mint condition expressed with units of degrees Celsius, and FBT$_4$ represents flexibility at a low temperature in aged condition expressed with units of degrees Celsius, fixing a range of values for the said characteristics, deriving the percentage of each polymer in the mixture, determining the influence of the percentage of the different polymers of said mixtures on at least one physical characteristic of the mixture, determining physical characteristics of the bitumen/polymers mixture to be obtained according to the polymers used by fixing the percentages of each polymer used, and producing a batch of roofing sealing material having a composition according to a selected one of said determined physical characteristics.

2. A process according to claim 1, further comprising the steps of:

producing at least four additional mixtures incorporating another polymer, measuring said physical characteristics for each of these additional mixtures, and revising the model of the said physical characteristics, to take into account the introduction of this another polymer.

3. A process according to claim 1, wherein the bitumen/polymers mixtures further comprises fillers.

4. A process according to claim 3, wherein the percentage of fillers is constant in each of the mixtures.

5. A process according to claim 1, wherein the physical characteristics of the mixtures are flexibility at low temperature in mint condition and in aged condition, Brookfield viscosity at 180° C., penetration at 25° C. and 60° C., and softening temperature.

6. A process according to claim 1, wherein the polymers of the said bitumen/polymers mixtures are selected from the group consisting of atactic polypropylene (APP), isotactic polypropylene (IPP) and the copolymers of the ethylene/propylene.

7. A process according to claim 1, further comprising the steps of:

establishing the influence of the percentage of each polymer on the said physical characteristics of the mixtures, and fixing the percentages of each polymer in order to derive the value of the said physical characteristics.

8. A process according to claim 1, further comprising the steps of:

establishing the influence of the percentage of each polymer of the mixture in said physical characteristics, fixing a range of values for the said characteristics and deriving the percentage of each polymer in the mixture.

9. A process according to claim 8, wherein the cost of each polymer is recorded.

10. A process according to claim 1, further comprising the steps of:

for one of said mixtures, establishing the influence of the percentage of the different polymers of said one mixture on the said physical characteristics, establishing target values of the said physical characteristics of one said mixture and calculating an additional quantity of at least one polymer to be added to said one mixture so that it exhibits physical characteristics of values more or less equal to said target values.

* * * * *